(12) United States Patent
Diekmann

(10) Patent No.: US 10,132,786 B2
(45) Date of Patent: Nov. 20, 2018

(54) METHOD FOR TESTING A GAS SENSOR AND GAS-MEASURING DEVICE WITH A TESTING DEVICE FOR TESTING A GAS SENSOR

(71) Applicant: Dräger Safety AG & Co. KGaA, Lübeck (DE)

(72) Inventor: Wilfried Diekmann, Utecht (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 58 days.

(21) Appl. No.: 15/460,680

(22) Filed: Mar. 16, 2017

(65) Prior Publication Data

US 2017/0269044 A1 Sep. 21, 2017

(30) Foreign Application Priority Data

Mar. 18, 2016 (DE) ........................ 10 2016 003 283

(51) Int. Cl.
*G01N 37/00* (2006.01)
*G01N 33/00* (2006.01)

(52) U.S. Cl.
CPC ....... *G01N 33/007* (2013.01); *G01N 33/0011* (2013.01); *G01N 33/0073* (2013.01); *G01N 2033/0072* (2013.01)

(58) Field of Classification Search
CPC ............. G01N 33/0006; G01N 33/007; G01N 27/4163; G01N 33/0011; G01N 33/0073; F02D 41/1495; F02D 41/222
USPC ........................................................ 73/1.06
See application file for complete search history.

(56) References Cited

U.S. PATENT DOCUMENTS

| | | | |
|---|---|---|---|
| 4,267,030 A | 5/1981 | Breuer et al. | |
| 4,338,281 A | 7/1982 | Treitinger et al. | |
| 4,854,155 A | 8/1989 | Poli | |
| 5,069,879 A * | 12/1991 | Leichnitz ............. | G01N 21/783 422/404 |
| 5,565,075 A | 10/1996 | Davis et al. | |
| 5,608,384 A * | 3/1997 | Tikijian ............... | G01N 27/626 324/464 |
| 6,182,497 B1 | 2/2001 | Krajci | |
| 7,406,854 B2 | 8/2008 | Lange et al. | |
| 7,645,367 B2 | 1/2010 | Tschuncky et al. | |
| 9,546,950 B2 * | 1/2017 | Schachinger .......... | G01N 21/31 |
| 2005/0247878 A1 | 11/2005 | Baschant et al. | |

(Continued)

FOREIGN PATENT DOCUMENTS

CH 624 488 A5 7/1981
DE 10 2006 045055 B3 2/2008

(Continued)

*Primary Examiner* — Eric S McCall
*Assistant Examiner* — Mohammed E Keramet-Amircola
(74) *Attorney, Agent, or Firm* — McGlew and Tuttle, P.C.

(57) ABSTRACT

A method for testing a gas sensor (30) and a gas-measuring device with a testing device for testing the gas sensor (30) make possible an improved analysis and evaluation of states of gas sensors (30). Due to the testing of a gas admission element (8) by monitoring measured signals (35, 38) in a time course (400) and a comparison with threshold values (350, 351) at predefined times (403, 404), (403", 404") in conjunction with the dispensing (91) of a quantity of test substance (5, 6), it is possible to test whether a gas supply (7) to the gas sensor (30, 309) is possible and given.

20 Claims, 6 Drawing Sheets

(56) References Cited

U.S. PATENT DOCUMENTS

| | | | | |
|---|---|---|---|---|
| 2009/0019913 A1* | 1/2009 | Gu | ..................... | G01N 33/0006 73/1.06 |
| 2013/0192332 A1 | 8/2013 | Scheffler et al. | | |
| 2013/0265579 A1* | 10/2013 | Beckmann | ............. | G01N 21/17 356/437 |
| 2014/0124672 A1* | 5/2014 | Stock | ................... | G01N 21/031 250/343 |
| 2014/0331737 A1* | 11/2014 | Kaneblei | ............ | G01N 33/0006 73/1.06 |
| 2017/0146501 A1* | 5/2017 | Martens | ............... | G01N 33/007 |

FOREIGN PATENT DOCUMENTS

| | | |
|---|---|---|
| DE | 20 2006 020 536 U1 | 11/2008 |
| DE | 10 2009 052 957 A1 | 6/2011 |
| EP | 1 281 957 A1 | 2/2003 |
| EP | 2 639 583 A1 | 9/2013 |
| EP | 2 887 062 A2 | 6/2015 |
| GB | 2 356 708 A | 5/2001 |
| WO | 99/17110 A1 | 4/1999 |
| WO | 02/091326 A1 | 11/2002 |

\* cited by examiner

METHOD FOR TESTING A GAS SENSOR AND GAS-MEASURING DEVICE WITH A TESTING DEVICE FOR TESTING A GAS SENSOR

CROSS REFERENCE TO RELATED APPLICATIONS

This application claims the benefit of priority under 35 U.S.C. § 119 of German Application 10 2016 003 283.9 filed Mar. 18, 2016, the entire contents of which are incorporated herein by reference.

FIELD OF THE INVENTION

The present invention pertains to a method for testing a gas sensor as well as to a testing device for testing the gas sensor of a gas-measuring device.

BACKGROUND OF THE INVENTION

Gas-measuring devices are used for industrial gas measurement and protect persons who are located in industrial areas or in buildings in which gases that are hazardous for health, be they process gases or waste gases, may be present, from risk to health and life.

Industrial gases are monitored by gas-measuring devices in industrial environments, for example, in the chemical or petrochemical industry, to determine whether these gases are associated with hazards based on explosive or toxic properties. Gas-measuring apparatus or gas-measuring devices used stationarily are used in many cases. Infrared-optical measuring sensors, electrochemical sensors, catalytic sensors or semiconductor gas sensors are usually used as sensors in such gas-measuring devices.

It is important for the reliability of the gas-measuring devices as well as of the alarms and warnings generated thereby, that the gas-measuring devices be fully able to function during the operation and that malfunctions be reliably detected.

A thin-layer semiconductor gas sensor is described in U.S. Pat. No. 4,338,281A. The thin-layer semiconductor gas sensor has an integrated heating element. It is a metal oxide semiconductor, in which the electrical resistance of the metal oxide semiconductor layer has a value that is dependent as a function of the concentration of the gas to be detected. This change in resistance can be measured as an indicator of the presence of the gas to be detected by a suitable electronic analyzing unit associated with the thin-layer semiconductor sensor.

A catalytically operating detector circuit for combustible gases is described in U.S. Pat. No. 4,854,155 A. The detectors for the combustible gases are configured as sensor resistor elements with a catalytic coating. Detectors for combustible gases are used to detect the presence of combustible gases that may occur, for example, in mines or industrial plants.

U.S. Pat. No. 5,565,075 A describes an electrochemical gas sensor for detecting nitrogen monoxide. In a housing filled with an electrolyte, the sensor has a working electrode, a reference electrode and a counterelectrode.

Such an electrochemical gas sensor can preferably be used for medical applications, because it has a low cross sensitivity to other gases usually used in this environment.

US 2005/0247878 A1 describes an infrared gas sensor. Two infrared radiation detectors arranged next to each other are arranged in a housing on one side of the housing, while a radiation source, which emits infrared radiation, is arranged on the other side. Gas to be analyzed is introduced into the beam path from a measuring environment.

The measurement effect is based on the fact that the light emitted by the radiation source is attenuated as a function of the gas species in the beam path. One of the two detectors is operated as a reference detector, while the other detector is operated as a measuring detector. The concentration of the gas introduced into the beam path is determined from the ratio of the signals of the measuring detector and of the reference detector.

In many application situations, such gas sensors are combined or developed into stationary gas-measuring devices. Stationary gas-measuring devices are often and usually distributed in industrial plants as a plurality of sensor units for gas measurement over a plurality of rooms or larger areas.

U.S. Pat. No. 6,182,497 B1 describes a gas-measuring system, which is configured to connect a plurality of sensors to a central analysis unit. The sensors may be connected, for example, via a universal, serial bus.

A gas sensor with an adapter is known from U.S. Pat. No. 7,406,854 B2. The adapter is configured for connecting a flexible tube. It is possible via this flexible tube to deliver gases from a remotely located measuring site or a measured gas or a calibrating gas to the gas sensor for testing the ability of the gas sensor to function. Measured gas or calibrating gas may be delivered, for example, by means of a feed pump.

WO 1999/17110 A1 as well as U.S. Pat. No. 7,645,367 B2 disclose gas-measuring systems comprising a gas sensor and a gas generator. Such combinations of gas generators and gas sensors make it possible to test the measuring properties of the gas sensors, especially to determine whether the gas sensor responds sensitively to the admission of a predefined measured gas concentration.

A device for testing a gas sensor is known, for example, from DE 20 2006 020 536 U1. A gas generator, which is suitable for generating ethane, is described there. The gas generator is intended for testing the gas sensor and is configured to dispense a certain quantity of a test gas to/into the gas sensor, and a resulting change or reaction of the output signal of the gas sensor represents an indication of the ability of the gas sensor to function.

The U.S. Occupational Safety Administration (OSHA) has recommendations for function tests with so-called "bump tests," in which a regular testing of gas sensors is to be performed by means of suitable adapters and a suitable test gas.

U.S. Pat. No. 7,406,854 B2 describes an adapter for testing or calibrating an electrochemical gas sensor. The adapter can preferably be placed on the gas sensor with a Velcro fastener and can be removed from same after completion of the testing or calibration.

There is a need for a regular testing of the ability of the gas sensors to function especially for already existing plants or installations of gas-measuring systems. In particular, there is a need for the testing of the gas sensors to be able to be performed without removal or disassembly of the gas sensors being necessary at the given measuring site in the plant. The testing of gas sensors in already existing gas-measuring systems shall be made possible without complicated manual operations performed by maintenance workers being necessary, for example, in case of the use of the adapter according to U.S. Pat. No. 7,406,854 B2, because it would otherwise be necessary for the maintenance workers in a larger industrial plant to mount the adapter for the subsequent testing of the sensors and then to remove the adapter manually when the gas sensor is put into operation. Furthermore, there is need for determining that gas sensors that deliver a gas concentration measured value as an output signal, from which the absence of harmful gases, i.e., a trouble-free situation, can be inferred, are indeed in an effective gas exchange with the measuring environment at the measuring site with the sensor-active elements. Consequently, there is a need for avoiding misinterpretations, especially of constant, noncritical gas concentration measured values or other constant output signals of the gas sensor.

SUMMARY OF THE INVENTION

With the knowledge of the above-mentioned state of the art, an object of the present invention is to provide a method for testing a gas sensor, which makes it possible to determine whether an unhindered admission of gas from a measuring environment to the gas sensor is possible.

Another object of the present invention is to provide a testing device, which makes it possible to carry out the method for testing a gas sensor.

Features and details that are described in connection with the method according to the present invention for testing the gas sensor also apply, of course, in connection with and in respect to the gas-measuring device suitable for carrying out the method and vice versa, so that reference is and can always mutually be made to the individual aspects of the present invention with respect to the disclosure.

The present invention is based on a test gas dispensing unit, which is arranged at a gas sensor in a gas-measuring arrangement or in a gas-measuring device, being operated so as to monitor or check whether an unhindered admission of gas into the gas sensor through at least one gas admission element, present in a gas-measuring arrangement or gas-measuring device, is occurring and thus to check whether the gas sensor is ready to operate.

Some of the terms used in connection with this patent application will be explained in more detail at the beginning.

An output signal or a measured signal, as well as a sensor signal is defined in the sense of the present invention as a signal which is provided by the gas sensor and which represents a gas concentration measured value. The output signal or the measured signal may be provided here by the gas sensor as a voltage signal, e.g., in a voltage range of 0 V to 10 V; a current signal, e.g., as a so-called 4-mA . . . 20-mA output signal; as digital data words by means of data lines and/or different interfaces and protocols, such as RS232, RS485, NMEA183, USB, CAN bus, LAN, WLAN, TCP/IP, Ethernet, Bluetooth.

A control signal is defined in the sense of the present invention as an individual control signal, a control signal as part of a set of control signals, as well as as a plurality or a set of control signals.

A data signal is defined in the sense of the present invention as an individual data signal, a data signal as part of a set of data signals, as well as a plurality or a set of data signals.

An output signal is defined in the sense of the present invention as an individual output signal, an output signal as part of a set of output signals, as well as as a plurality or a set of output signals. A data link is defined in the sense of the present invention as a connection of at least two participants by means of a wired, wireless, optical connection, which is suitable for transmitting output signals, control signals, data signals or output signals. Both direct physical connections (cable connections, radio connections, light guide connections), as well as indirect or logic connections for transmitting information, control signals, data signals or output signals with physical or data technical conversions or transformations of signals, voltages, currents are covered.

A measured gas is defined in the sense of the present invention as a gas or a gas mixture that is such that the at least one gas sensor is sensitive to a change in a gas concentration of this measured gas and responds to changes in the gas concentration of this measured gas with changes in the gas concentration measured value.

A test gas is defined in the sense of the present invention as a gas or a gas mixture that is such that the at least one gas sensor is sensitive to a change in a concentration of this gas or gas mixture and responds to changes in the concentration of this test gas with changes in the gas concentration measured value.

A quantity of a test substance is defined in the sense of the present invention as a quantity of a fluid in the liquid, gaseous or liquid-gaseous phase, which can be converted into a test gas in the sense of the present invention by vaporization, atomization, nebulization, evaporation or by means of a change in pressure, especially by decompression by means of pressure reduction.

The provision of a possibility of checking according to the present invention whether unhindered admission of gas into the gas sensor is given through the at least one gas admission element enables the user, e.g., the maintenance workers, especially in larger industrial plants, to perform a check/testing of the readiness of gas sensors to operate without major personnel expenditure in terms of work time, and hence especially and preferably also routinely.

An unimpeded supply (flow/diffusion) of gas is a basic requirement for an output signal of the gas sensor, which signal is a noncritical gas concentration, a zero (null) signal, i.e., a complete or nearly complete absence of a harmful gas, to be also able to be correctly interpreted by the user as a noncritical situation. A situation in which the zero signal is outputted as an output signal of the gas sensor, even though the at least one gas admission element does not allow unhindered supply of gas (ambient/environmental gas) into the gas sensor, is problematic.

A test gas dispensing unit is therefore arranged according to the present invention downstream of the at least one gas admission element in the gas-measuring arrangement (between the (at least one) gas admission element and a sensor measuring arrangement). The test gas dispensing unit is configured to dispense or to allow to flow a liquid phase, a gaseous phase or a liquid-gaseous phase of a quantity of a test substance from a test substance reserve (container, test substance reservoir or test gas reservoir, tank) to the sensor-measuring arrangement arranged in the gas sensor. The sensor-measuring arrangement is configured to detect a gas concentration or a change in a gas concentration.

A test substance reserve is defined in the sense of the present invention as a container for storing and providing the quantity of test substance, i.e., a fluid in the liquid, gaseous or liquid-gaseous phase. The test substance reserve is configured as a tank, test substance reservoir, test gas reservoir, test fluid reservoir or container (cylinder), the quantity of test substance being stocked, stored and made available for dispensing in the test substance reserve by means of the test gas dispensing unit in the gaseous form under pressure or in the liquid state of aggregation under ambient pressure, as well as in a combined liquid/gaseous state, at least partly under pressure, for example, in the form of a liquefied gas cylinder (propane, butane).

The following may be mentioned here as some of the examples for sensor-measuring arrangements in different types of gas sensors:

Electrode/electrolyte combinations in electrochemical gas sensors, radiation source/detector element combinations in infrared optical gas sensors, catalytically active and/or catalytically passive measuring elements in catalytic gas sensors or in heat tone sensors (pellistors), field effect transistors with gas species-sensitive semiconductor elements, for example, gas species-sensitive gate substrates in semiconductor gas sensors.

For example, gas generators or configurations of the test substance reserve or configurations of tank type containers combined with valves, switching means or piezo dispensing elements, which are operated, checked, controlled or regulated by a control unit such that defined quantities of test gas or a defined quantity of test substance can be sent or fed to the gas sensor in the liquid or gaseous form, are suitable configuration possibilities for embodying test gas dispensing units.

A memory for providing predefined durations, measured signal threshold values, comparison criteria or comparison variables are associated with the control unit, or the memory is also contained as an element in the control unit.

For example, dispensing by means of time intervals or durations, whose beginning and end are defined by the control unit, makes it possible to set the quantity of test substance reproducibly and accurately, especially if this quantity of test substance is being stored in the test substance reserve under a defined and known pressure.

The quantity of test substance or the test gas is preferably fed into the gas sensor by means of the test gas dispensing unit in the liquid form, because stocking or storage in the liquid form in the test substance reserve has the advantage of placing, in a relatively small volume, close to the gas sensor, a quantity of test substance that is sufficient for the duration of the use (service life) of the gas sensors. Such a storage is known, for example, from gas lighters, in which butane is used as a liquefied gas. The gas sensor or the gas-measuring arrangement have according to the present invention at least one sensor-measuring arrangement for detecting a gas concentration or a change in a gas concentration. The gas sensor has a suitable configuration by means of the sensor-measuring arrangement and is intended for the qualitative as well as quantitative analysis of gases or gas mixtures fed to this gas sensor from the measuring environment by means of a gas inlet. In addition, the at least one gas admission element, the test gas dispensing unit and the control unit are arranged at or associated with the gas sensor or the gas-measuring device.

The at least one gas admission element is arranged at the gas sensor at the gas inlet or at a gas inlet of the gas-measuring device such that air, gases or gas mixtures from the measuring environment must first pass through the gas admission element to reach the sensor-measuring arrangement in the gas sensor. The feed preferably takes place through the gas admission element by means of diffusion. The at least one gas admission element is configured, for example, as a semipermeable or permeable membrane, a protective grid or a flame protection disk or sintered disk and acts functionally as a diaphragm, as a protection against the entry of contaminants or moisture into the gas sensor, on the one hand, and also as an explosion protection in the embodiment as a flame protection disk. This at least one gas admission element is arranged upstream (with respect to a diffusion flow path) of the sensor-measuring arrangement for carrying out the above-described functional actions.

An embodiment of the gas sensor or of the gas-measuring arrangement or of the gas-measuring device with a plurality of gas admission elements appears, for example, in a constellation with a plurality of gas sensors in a gas-measuring arrangement or gas-measuring device such that each of the plurality of gas sensors has at least one gas admission element arranged directly at the respective gas inlet of the gas sensor, configured, for example, as a diaphragm, upstream of the respective sensor-measuring arrangement, and, in addition, an additional gas admission element, configured, for example, as a protective grid or flame protection disk, is arranged at a central gas inlet of the gas-measuring arrangement or gas-measuring device.

The test gas dispensing unit may be arranged in such an embodiment according to the present invention both downstream of one of the gas admission elements arranged directly at the respective gas inlet of one of the gas sensors and downstream of the additional gas admission element, i.e., upstream of one of the gas inlets and of the respective corresponding gas admission elements of the gas sensors in the gas-measuring device. The test gas dispensing unit is arranged in both cases in the course of the incoming flow between the gas admission element or gas admission elements and one of the sensor-measuring arrangements in the gas-measuring device. The flow directions—upstream as well as downstream—are defined by the incoming flow of gas from the measuring environment in the direction of the gas sensor or in the direction of the gas-measuring device towards the sensor-measuring arrangements.

The method according to the present invention for testing the at least one gas admission element of the gas sensor or for testing the at least one gas admission element of a gas-measuring device with at least one gas sensor is carried out according to a first aspect of the present invention by means of a sequence of operating states controlled by a control unit from a start time, beginning with a first operating state with a continuous measuring operation, such that the control unit brings about in a second operating state a dispensing of a quantity of test substance by means of the test gas dispensing unit arranged downstream of the gas admission element and upstream of the sensor-measuring arrangement in the gas sensor, the control unit initiates the start of an expectancy time window in a third operating state, the control unit detects at least one measured signal or a plurality of measured signals of the gas sensor with the start of the expectancy time window and the control unit compares the at least one detected measured signal or one of the plurality of measured signals with a first measured signal threshold value, the control unit detects at least one additional measured signal or an additional plurality of measured signals of the gas sensor in a fourth operating state, and the control unit compares the at least one additional detected measured signal or one of the additional plurality of measured signals with a second measured signal threshold value, and the control unit initiates the end of the expectancy time window, in a fifth operating state, the control unit determines on the basis of the comparison of the measured signal with the first measured signal threshold value and/or with the second measured signal threshold value whether the gas admission element is ready to function for feeding air, gas or gas mixture from a measuring environment and determines an indicator for the readiness of the gas sensor and/or of the gas-measuring device with at least one gas sensor to operate.

The method according to the present invention makes it possible to perform a testing from the continuous measuring operation in the first operating state at regular time intervals, for example, in a time rhythm, of 24 hours to several days or weeks, which rhythm can be selected in the gas-measuring device or at the gas sensor, to determine whether unhindered admission of gas from the measuring environment is guaranteed to the gas-measuring device or to the gas sensor.

The continuous measuring operation represents, so to speak, the regular operating state of the gas-measuring device as well as the regular operating state of the gas sensor and can be configured as a continuous, ongoing or routine detection of measured signals, a detection of measured signals controlled in time by means of a detection rate (scanning rate), for example, at a detection rate that corresponds to a measured signal detection of a predefined number of measured signals per second or minute, or it may be configured as a measured signal detection in which the detection of a predefined number of measured signals is initiated by an event or by a trigger.

The testing according to the present invention of the supply from the measuring environment or the permeability to gas of the gas admission element represents according to the present invention only an interruption of the continuous measuring operation for a short time of usually less than one minute.

The second operating state is the operating state which begins by a dispensing of the quantity of test substance downstream of the gas admission element and upstream of the sensor-measuring arrangement, i.e., at a location that is located between the gas admission element and the sensor-measuring arrangement. The dispensing thus takes place in the interior of the gas sensor. The quantity of test substance dispensed at this location in the interior of the gas sensor at a first time $t_1$ then reaches the sensor-measuring arrangement as a test gas, as an incoming test gas flow, and if the gas admission element is permeable to the test gas being dispensed, it is again discharged through the gas admission element as an outgoing test gas flow, i.e., from the gas sensor, into the measuring environment. The duration, beginning with the dispensing of the quantity of test gas or beginning with the incoming test gas flow to the sensor-measuring arrangement for a duration which corresponds to the sum of the duration of the incoming test gas flow to the arrangement and of the outgoing test gas flow into the measuring environment, is called the process time.

The third operating state is an operating state which follows in time the dispensing of the quantity of test gas, which takes place in the second operating state, and the process time, which begins with the dispensing of the incoming test gas flow or which at least partially overlaps in time with the process time and initiates the beginning of an expectancy time window. With the beginning or at the start of the expectancy time window, at least one measured signal or a plurality of measured signals are detected at a third time $t_3$ and compared with a first measured signal threshold value.

At least one additional measured signal or an additional plurality of measured signals are detected and compared with a second measured signal threshold value in the fourth operating state in the course of the expectancy time window at a fourth time $t_4$ before or at the time of the initiation of the end of the expectancy time window. The start and the end of the expectancy time window, the values of the first and second measured signal threshold values as well as the location in time of the times for the signal comparison (third time $t_3$, fourth time $t_4$) in the expectancy time window are preferably derived from a previously determined, typical signal characteristic of the gas-measuring device and the conditions (quantity, time characteristic, concentration) of the dispensing of the quantity of test substance. Preferably also included in this are the response characteristics (rise time, e.g., $t_{10-90}$ rise time, decay time, e.g., $t_{90-10}$ decay time), the course of the signal amplitude with zero signal and maximum signal amplitude in case of unhindered incoming flow through the gas admission element to the gas-measuring device and unhindered outflow into the measuring environment through the gas admission element.

A value with a signal amplitude that is lower than the value of the first measured signal threshold value is selected here as the value of the second measured signal threshold value. These dimensionings of the first and second measured signal threshold values arise from the fact that there is a decay in the measured signal during the expectancy time window in case of unhindered outflow of the quantity of test substance being dispensed from the gas sensor through the gas admission element into the measuring environment.

A test is performed in the fifth operating state to determine whether the gas admission element is able to function for feeding air, gas or gas mixture from the measuring environment. If both the comparison in the third operating state and the comparison in the fourth operating state show that the actual value was below both measured signal threshold values, gas exchange with the measuring environment is possible and the gas admission element is therefore able to function for feeding air, gas or gas mixture from the measuring environment. The control unit determines the indicator for the readiness of the gas sensor and/or of the gas-measuring device with at least one gas sensor to operate on the basis of the comparisons.

Provisions are made in a special embodiment for the gas-measuring device to provide a substitute signal for the duration of the interruption. This is used to avoid possible misinterpretations of the measured data on a display element or at a data interface, for example, in the form of triggering a gas concentration alarm. Such a substitute signal may be, for example, a chronologically preceding measured signal or a signal that is derived from one or more chronologically preceding measured signals and which is provided by means of an output unit. However, a status signal may also be provided from the output unit as a substitute signal, which indicates for the duration of the testing of the gas admission element that the gas-measuring device or the gas sensor is not currently ready for measuring gases from the measuring environment.

In a preferred embodiment, the dispensing of the quantity of test substance from the test gas dispensing unit to the sensor-measuring arrangement in the gas sensor is brought about by the control unit in the second operating state such that the control unit activates the test gas dispensing unit in the time course at a first time (activation time) $t_1$. This activation is configured, for example, as the switching on of a valve with an electrical control signal.

The dispensing of the quantity of test substance is preferably brought about in this preferred embodiment as a dispensing in the form of a quantity of liquid test substance. This quantity of test substance dispensed in the liquid form will then change over into the gaseous phase in the gas sensor after the dispensing, for example, due to evaporation or atomization brought about by an impact on a wall arranged in/at the gas sensor.

One possibility of embodying the dispensing in the second operating step is given by embodying the test gas dispensing unit as a piezo dispensing element combined with the test substance reserve. Such a piezo dispensing unit is configured to dispense an exactly defined quantity of test substance in case of a single-time activation. The dispensing of the exactly defined quantity of test substance takes place here without deactivation being necessary for setting the dispensed quantity of test substance. A piezo dispensing element operates according to the piezoelectric effect, where a deformation takes place in the piezo material, for example, ceramic, on activation by an electrical voltage pulse. An extrusion pressure corresponding to this deformation results from the deformation. The defined quantity of test substance is dispensed with the pressure through a fine nozzle. The use of such piezo dispensing elements or piezo ceramic dispensing elements is known, for example, from the field of printing technology (ink jet printers) as a so-called ink jet technology.

Another alternative possibility of embodying the dispensing in the second operating step is given by embodying the test gas dispensing unit as a combination of a heating element suitable for the evaporation of the quantity of liquid test substance with the test substance reserve. It is possible to generate a defined quantity of test substance by means of the heating element with a single-time activation (heating pulse). Acetone or ethyl alcohol shall be mentioned here as an example for a suitable quantity of a liquid test substance. The dispensing of the exactly defined quantity of test substance is carried out here by forming a vapor bubble in an explosion-like manner, without deactivation being necessary for setting the dispensed quantity of test substance. The use of such heating elements is known, for example, from the field of printing technology (ink jet printers) under the term bubble jet.

If, for example, a quantity of liquid test substance, for example, of butane or propane, is dispensed in the second operating state, for example, at the time $t_1$, the quantity of liquid test substance evaporates and it is available at a time $t_1'$ as a quantity of gaseous test substance at the sensor-measuring arrangement in the gas sensor. This quantity of gaseous test substance brings about in the gas sensor a reaction of the sensor-measuring arrangement in the form of a change in the gas concentration measured value as an output signal.

If the gas sensor is configured, for example, as an electrochemical gas sensor, a change will occur in the measured signal or output signal because of chemical and/or electrochemical reactions in/at the sensor-measuring arrangement.

If the gas sensor is configured, for example, as an infrared optical gas sensor with a measuring cuvette, an attenuation of the propagation of light will take place in the measuring cuvette to the sensor-measuring arrangement and a change in the output signal will take place in a wavelength range of the optical gas sensor due to the absorption properties of the test gas. If the gas sensor is configured, for example, as a catalytic gas sensor, a change will take place in the output signal because of combustion reactions and/or chemical reactions at the measuring element (pellistor) as a sensor-measuring arrangement with the quantity of gaseous test substance.

If the gas sensor is configured, for example, as a semiconductor gas sensor, a change will take place in the output signal because of chemical reactions at the gas species-sensitive semiconductor elements of the sensor-measuring arrangement.

In a preferred embodiment, the dispensing of the quantity of test substance by the test gas dispensing unit to the sensor-measuring arrangement in the gas sensor is brought about by the control unit in the third operating state such that the test gas dispensing unit is activated at a first time (activation time) $t_1$ and deactivated at a second time (deactivation time) $t_2$.

The test gas dispensing unit dispenses a quantity of test substance predefined—indirectly by the time interval—for a predefined time interval ($\Delta t_{dispensing} = t_2 - t_1$) until the second time (deactivation time) $t_2$ to the sensor-measuring arrangement in the gas sensor.

The second time (deactivation time) $t_2$ is obtained as a time distanced in time from the first time (activation time) $t_1$ due to the deactivation of the test gas dispensing unit by means of the control unit. A configuration with activation and deactivation is ideal and practicable, for example, in advantageous embodiments of electrical switching signals in conjunction with the test gas dispensing unit with one or more electrically controlled valves.

The predefined quantity of test substance is determined by the predefined time interval in conjunction with the predefined general conditions, such as the pressure prevailing in the test substance reserve, temperature and an opening cross section of a valve used for the activation and deactivation. Such a predefined quantity of liquid test substance is also called a bolus or bolus quantity. Many different types of valves suitable for dispensing fluids or liquids, such as digital on-off valves with binary states (normally open (NO) or normally closed (NC)) or also proportional valves may be used as valves in the test gas dispensing unit.

Another embodiment with activation and deactivation is practicable as a test gas dispensing unit, for example, in the form of electrical setting signals for gas generation by means of one or more gas generators.

In a special embodiment, a size and/or a volume of the gas sensor is taken into account by the control unit for the determination of the second time (deactivation time) $t_2$ in the time course t (the determined second time is a function of the size and/or a volume of the gas sensor). Taking the variable and/or the volume of the gas sensor into account makes it possible to take into account different sizes or volumes of gas sensors, which lead to different inflow conditions and inflow quantities. By selecting the second time (deactivation time) $t_2$, a quantity of test substance that is adapted to the size and volume can be dispensed in this manner by the test gas dispensing unit by means of the control unit.

In another preferred embodiment, a size and/or volume of the gas sensor is taken into account by the control unit when determining the portion of the liquid test substance by means of the test gas dispensing unit as well as when dispensing the portion of liquid test substance (the portion and the timing of dispensing the portion are a function of the size and/or volume of the gas sensor). The portion of the liquid test substance is correspondingly adapted in this embodiment to the size and/or the volume of the gas sensor, and an adapted bolus of the quantity of test substance, which corresponds to the size and/or the volume of the gas sensor, is determined by the control unit and dispensed by means of the test gas dispensing unit.

In another preferred embodiment, the third time $t_3$ is derived in the third operating state by the control unit from the first time (activation time) $t_1$ in the time course or from a time $t_1'$ derived from this first time (activation time) $t_1$. The first time (activation time) $t_1$ is representative of the dispensing of the quantity of liquid test substance to the sensor-measuring arrangement in the second operating state. The third time $t_3$ is derived from the first time (activation time) $t_1$ such that the third time $t_3$ is distanced in time from the first time $t_1$ or from the time $t_1'$ such that the process time corresponds to a duration during which an unhindered inflow from the measuring environment through the gas admission element to the sensor-measuring arrangement into the gas sensor corresponds to a subsequent unhindered outflow from the gas sensor into the measuring environment or is corresponding to this process time.

A size and/or a volume of the gas sensor, a number, a thickness, a pore size, an area and/or a diameter of the gas admission element is taken into account by the control unit in an especially preferred embodiment for determining the duration of the process time and/or for the third time $t_3$ in the time course t (the duration of the process time is a function of the size and/or a volume of the gas sensor, a number, a thickness, a pore size, an area and/or a diameter of the gas admission element).

In an especially preferred embodiment, a size and/or a volume of the gas sensor, a number, a thickness, an area and/or a diameter of the gas admission element is taken into account by the control unit for determining the duration of the expectancy time window and/or for determining the fourth time $t_4$ in the time course t (the duration of the expectancy time window and/or for determining the fourth time $t_4$ in the time course t are a function of a size and/or a volume of the gas sensor, a number, a thickness, an area and/or a diameter of the gas admission element). Taking into account the size and/or the volume of the gas sensor as well as the number, thickness, pore size, area and/or diameter of the gas admission element when determining the process time or when determining the duration of the expectancy time window makes it possible to adapt the testing of the gas sensor to the particular gas sensor constellation in the gas-measuring arrangement or gas-measuring device, because the number, thickness, area or diameter, pore size of the gas admission element are essential factors determining the velocity of the gas supply by diffusion as well as the velocity of outflow of the gas by diffusion.

In another preferred embodiment of the method, a status signal is determined and/or provided by the control unit on the basis of the comparison in the fifth operating state. The comparison in the fifth operating state yields the result showing whether a dispensed quantity of test substance within the expectancy time window will flow or diffuse out of the gas sensor through the gas admission element. If the diffusion from the gas sensor or the outflow from the gas sensor does not take place within the duration of the time window, a status signal, which shows that the gas sensor or the gas-measuring arrangement is not able to function correctly may be generated by the control unit.

It can be determined from the situation that a dispensed quantity of test substance has not left the gas sensor through the gas admission element, that the flow from the measuring environment into the gas sensor through the gas admission element is not optimal, either or may even be impossible due to a blockage.

In another preferred embodiment, the status signal is provided by the control unit for the output unit, a central analysis system, a central alarm unit or a mobile output device. Such provision for an output unit, a central analysis system, a central alarm unit or a mobile output device, for example, a mobile telephone or another mobile communication device, makes it possible to communicate the status of the gas sensor or of the gas-measuring arrangement to additional external locations. Suitable data links to additional external locations (0-10 V, 4-20 mA, Ethernet, LAN, W-LAN, USB, RS232, etc.) are provided for this for connecting the control unit to the output unit as well as to the central analysis system or to the central alarm unit or to the mobile output devices. The data links are configured to transmit measured data as well as gas concentration values, alarm signals or even unwanted signals to the output unit, the central analysis system, the central; alarm unit or mobile output devices.

An alarm signal or a message is outputted by the output unit, the central analysis system, the central alarm unit or the mobile output devices in another embodiment.

In another preferred embodiment, the alarm signal is provided by the control unit and/or the output unit for an acoustic alarm generator for generating an acoustic alarm and/or to an optical signal generator for generating a visual, visible alarm.

The embodiments described represent, both in themselves and combined with one another, special embodiments of the method according to the present invention for testing the gas sensor or the gas-measuring device, especially the gas admission element. Advantages and additional embodiments arising through a combination or combinations of a plurality of embodiments are likewise covered by the inventive idea, even though not all possibilities of combining embodiments for this are explained in detail. The above-described embodiments of the method may also be configured in the form of a computer-implemented method as a computer program product with a computer, in which case the computer is prompted to execute the above-described method according to the present invention when the computer program or parts of the computer program are executed on the computer or on a processor of the computer or on a so-called "embedded system" as part of a gas-measuring device, gas sensor or gas-measuring arrangement or on a—preferably computer-assisted—analysis system associated with the gas sensor or the gas-measuring arrangement. The computer program may also be stored on a machine-readable storage medium. In an alternative embodiment, it is possible to provide a storage medium that is intended for storing the above-described, computer-implemented method and can be read by a computer. It is within the scope of the present invention that all the steps of the method or of the computer program do not necessarily have to be executed on one and the same computer, but they may also be executed on different computers. The sequence of the method steps may possibly be varied as well.

The accomplishment of the object was described above with reference to the method claimed as the first aspect of the present invention. Features, advantages or alternative embodiments mentioned in this connection may likewise be extrapolated to the subjects claimed according to another aspect of the present invention and vice versa. The corresponding functional features of the method may be configured according to the invention by corresponding physical modules or units of a device, especially by hardware components (µC, DSP, MP, FPGA, ASIC, GAL), which may be implemented, for example, in the form of a processor, a plurality of processors (µC, µP, DSP) or in the form of instructions in a memory area, which are processed by the processor.

Another aspect of the present invention thus arises, which accomplishes the objects set according to the present invention by a device for carrying out the method for testing a gas sensor and by a gas-measuring device with a testing device for testing the gas sensor. This device, suitable for carrying out the method, is configured such that the testing of the gas sensor and/or of the gas-measuring device or gas-measuring arrangement is carried out according to the steps described in the method and the additional steps described in the embodiments are also carried out each in itself or combined.

The gas-measuring device according to the present invention with a testing device for carrying out the method has for this at least one gas sensor with a gas admission element, with at least one sensor-measuring arrangement, with a test gas dispensing unit, a control unit and a memory associated with the control unit. The processing and the control of the operating states are carried out by means of the control unit. The measured signal detection, the control of dispensing, the storage of measured signals, the comparisons of the measured signals with threshold values and the determination of the indicator for the readiness of the gas sensor to operate are controlled by the control unit, partly in conjunction with the memory. The gas admission element is arranged upstream of the sensor-measuring arrangement in the gas sensor or in the gas-measuring arrangement, and the test gas dispensing unit is arranged downstream of the gas admission element in the gas sensor or in the gas-measuring arrangement.

In one embodiment, the test gas dispensing unit is configured as a piezo dispensing element and a reservoir fluidically connected to the piezo dispensing element. The reservoir, for example, in the form of a tank, is configured for stocking a test substance reserve. The control unit is configured to activate the piezo dispensing element at a first time $t_1$ in order to bring about the dispensing of a quantity of test substance, which is being stocked in the test substance reserve, to the gas sensor or to the gas-measuring arrangement.

In a preferred embodiment, the test gas dispensing unit is configured by a valve in conjunction with a reservoir fluidically connected to the valve. The reservoir is configured, for example, as a tank for storing or stocking a test substance reserve. The control unit is configured to bring about an activation of the valve at a first time $t_1$ and a deactivation of the valve at a second time $t_2$ in order to bring about the dispensing of a quantity of test substance from the test substance reserve to the gas sensor or to the gas-measuring arrangement. As a result, the activation and deactivation preferably take place by means of electrical switching signals, which can be transmitted by the control unit to the test gas dispensing unit.

In an especially preferred embodiment, the gas-measuring device has an output unit, an optical alarm generator or an acoustic alarm generator. The optical alarm generator and/or the acoustic alarm generator are configured and provided, in cooperation with the control unit and/or with the output unit, to output an alarm signal. The gas-measuring device additionally has here an optical interface, which is configured and provided in cooperation with the control unit to transmit a status signal to an analysis system.

In another preferred embodiment, the sensor-measuring arrangement is configured as a combination of electrodes and an electrolyte in an electrochemical gas sensor, as a combination of a radiation source and of a detector element in an infrared optical gas sensor, as a combination of catalytically active and/or catalytically passive measuring elements in a catalytic gas sensor, or in a heat tone sensor, as well as as gas species-specific and sensitive semiconductor elements in a semiconductor gas sensor.

With the method for testing a gas sensor and with the gas-measuring device with a testing device for testing a gas sensor, the present invention provides an advantageous possibility, which can technically very easily be embodied, for the reliable determination of whether an unhindered admission of gas is possible through the gas admission element into the gas-measuring device or to the gas sensor.

In addition, another advantage is that it is also possible to test the function of the gas sensor itself, as well as the dispensing of the quantity of test substance proper by means of the method of dispensing the predefined quantity of test substance. This arises from the fact that the measured signal shows no change even if either the sensor-measuring elements in the gas sensor do not function as intended or are defective, or if the dispensing of the predefined quantity of test substance does not function properly. This leads to the advantage that in addition to the testing of the gas admission elements belonging to the gas sensor or the gas-measuring device, it is possible to test both the testing device with the function of dispensing the quantity of test substance proper and the function of the gas sensor or of the gas-measuring device or of the sensor-measuring elements and elements for signal processing with the method for testing a gas sensor and with the gas-measuring device with a testing device for testing a gas sensor. This leads, on the whole, to the advantage that no possible situation, in which a malfunction of one or more of the essential components of the gas sensor or of the gas-measuring arrangement with a gas sensor, i.e., gas admission element or the sensor-measuring elements, as well as of the elements (supply lines, electronic units, amplifiers, A/D converters) for signal processing, which components and elements are essential for a reliable, safe and high-quality operation, will essentially remain unnoticed.

A special advantage arises additionally, namely, that it is also possible to detect a possible malfunction of the test gas dispensing unit, for example, a possible blockage or leakage during the feed of the quantity of test substance or of the valve provided for dispensing, a disturbance in the electrical control of the valve (e.g., signal error, line break, broken wire) or an empty test substance reserve. These causes of error cannot be differentiated and distinguished from one another in all cases, and the advantage arises for the use that arrangements for gas measurement and gas sensors that are able to function can be clearly distinguished from malfunctioning devices and gas sensors.

The present invention will be explained in more detail by means of the following figures and the corresponding descriptions of the figures without limiting the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
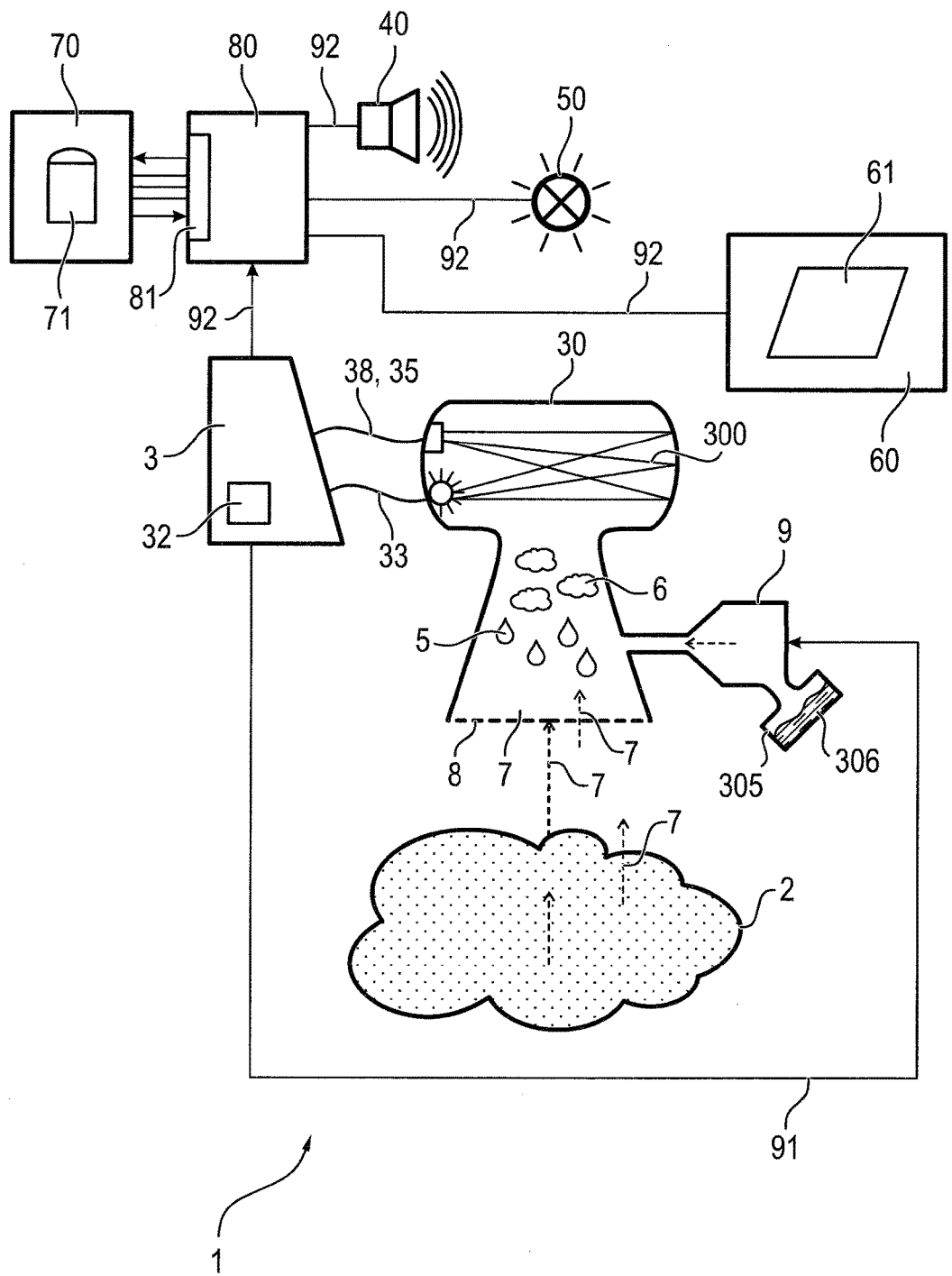
FIG. 1a is a schematic view of a gas-measuring arrangement with an optical gas sensor and with a testing device.
Figure 1B:
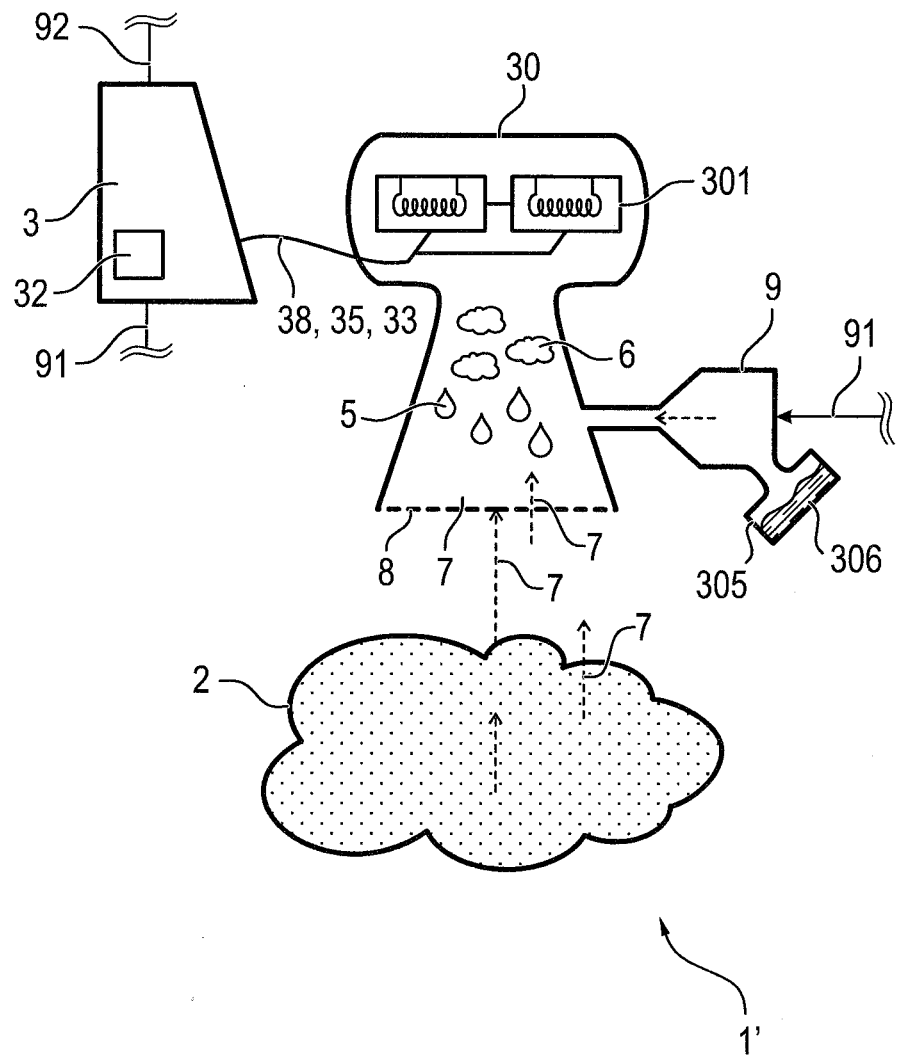
FIG. 1b is a schematic view of a gas-measuring arrangement with a catalytic gas sensor and with a testing device.
Figure 1C:
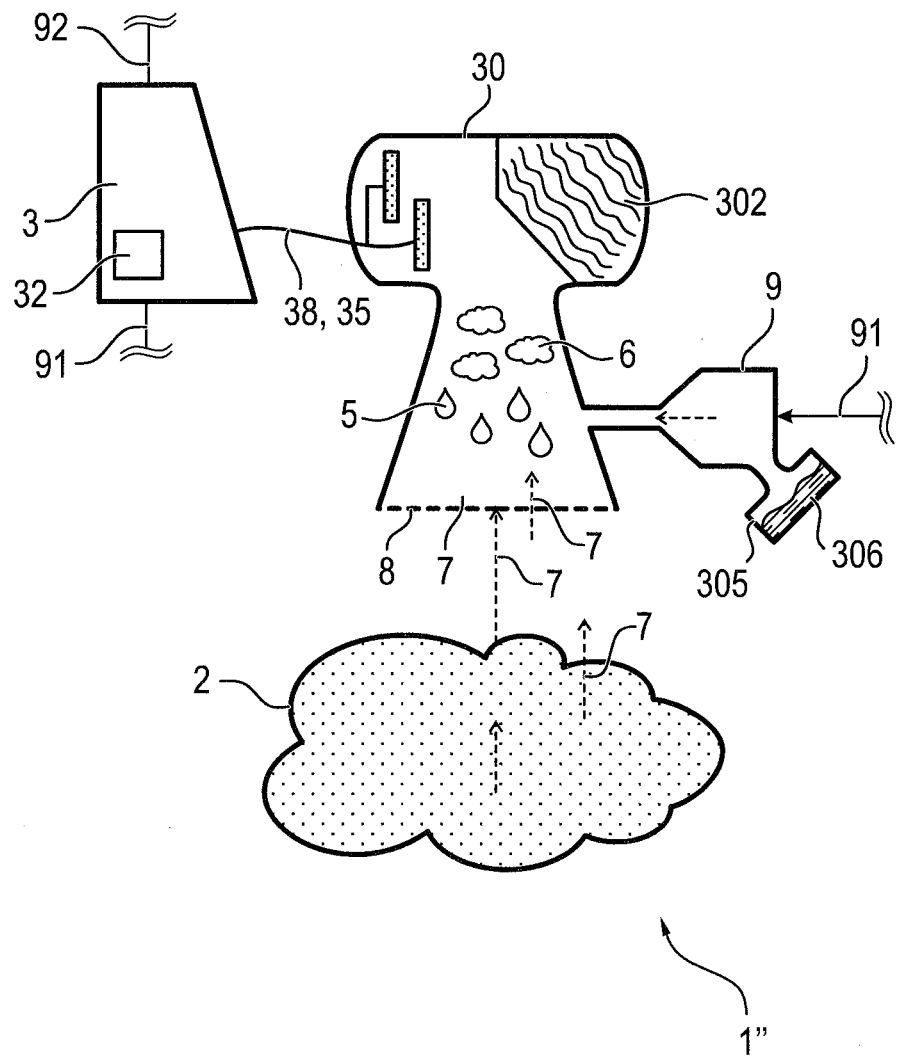
FIG. 1c is a schematic view of a gas-measuring arrangement with an electrochemical gas sensor and with a testing device.

Referring to the drawings, FIGS. 1a, 1b, 1c as well as 1d show arrangements for gas measurement with a gas sensor and with a testing device. FIG. 1a shows a gas-measuring arrangement 1 with an optical gas sensor 300. The optical gas sensor 300 is configured as a cuvette with a multireflection cell, not shown in detail in this FIG. 1a for reasons of clarity. A radiation source and a detector element are arranged as a sensor-measuring arrangement in the multireflection cell. Light is radiated in the multireflection cell from the radiation source onto an opposite wall as well as to side walls, reflected from there and detected by the element after multiple reflections. The presence of a test gas to be measured, for example, methane, ethane, butane, propane, changes the absorption for the emitted light in the infrared wavelength range. This can be detected as a measurement effect of an attenuated signal on the detector element. The measurement effect of an attenuation of the emitted IR light by certain gases, for example, methane, ethane, butane, propane, and other hydrocarbons is thus obtained. The gas from a measuring environment 2 enters the optical gas sensor 300 via a gas admission element (gas inlet) 8, for example, a semipermeable or permeable diaphragm, a protective grid or a flame protection disk, entering the measuring cuvette of the optical gas sensor 300. Only a single gas admission element 8 is shown in this FIG. 1a as an embodiment of the environmental/ambient gas supply 7 with a gas admission element 8.

Figure 1D:
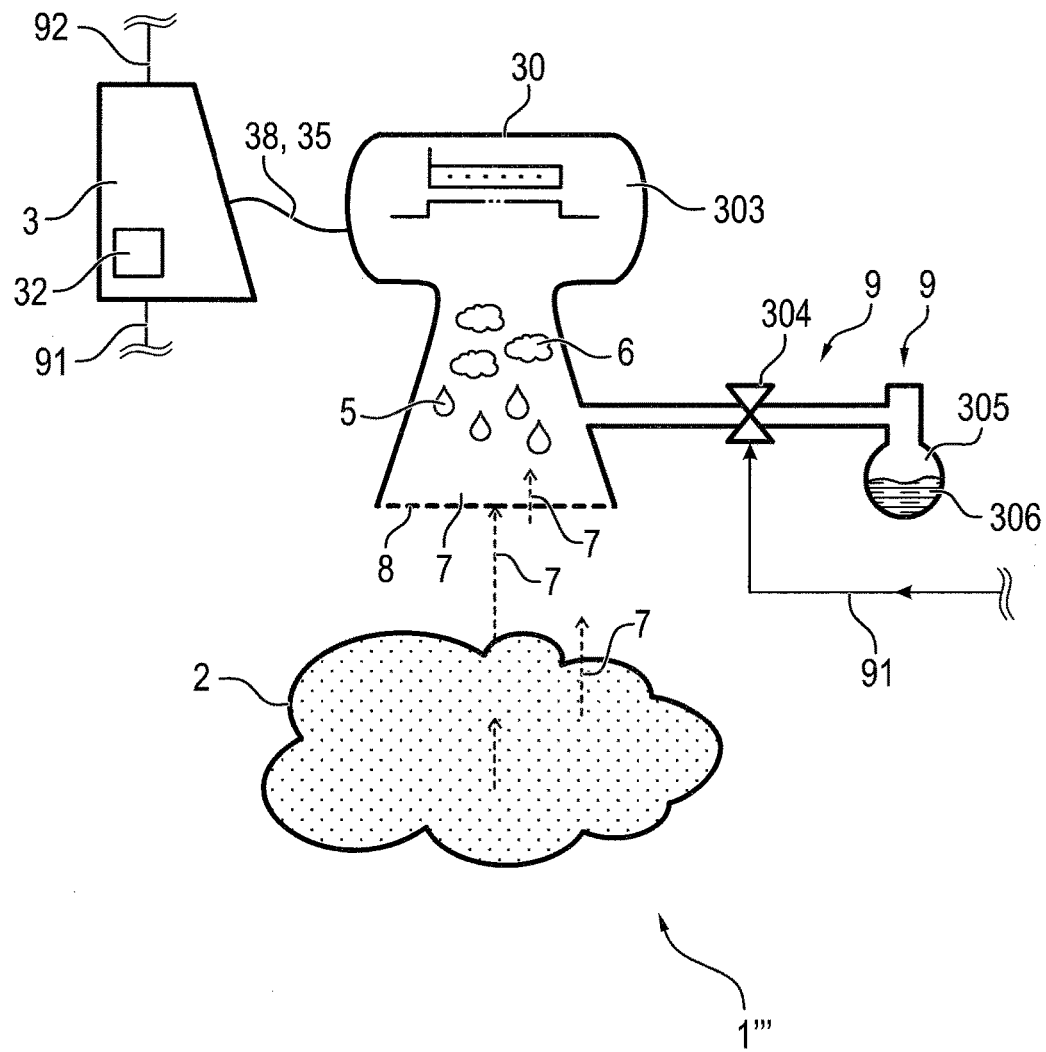
FIG. 1d is a schematic view of a gas-measuring arrangement with a semiconductor gas sensor.

In an embodiment of a gas-measuring arrangement 1 in a device in which a plurality of gas sensors are arranged as a gas sensor system 30, it is technically common and advantageous in many technical embodiments to provide a plurality of gas admission elements 8 arranged one after another in a row. It is thus conceivable that, downstream from the measuring environment 2, a first gas admission element acts as a flame protector or dust protector, followed by a second element preventing the entry of moisture and a third element 8 in the gas sensor proper protects, for example, the optical gas sensor 300 or a catalytic gas sensor 301 (FIG. 1b) or an electrochemical gas sensor 302 (FIG. 1c) or a semiconductor gas sensor 303 (FIG. 1d). The test gas dispensing unit 9 may be arranged both downstream of the measurement between the first and second gas admission elements, between the second and third gas admission elements 8 or between the third gas admission element 8 and the gas sensor system 30, 300. These embodiments with a plurality of gas admission elements and possible, suitable positions in which the test gas dispensing unit 9 is arranged are not shown in the gas-measuring arrangement 1 for the sake of clarity of this FIG. 1a. However, these possible embodiments are also covered in the sense of the present invention as arrangements of the test gas dispensing unit 9 at the gas sensor system 30. Such a gas supply (supply of environmental/ambient gas) 7 takes place from the measuring environment 2 towards the optical gas sensor 300.

A test gas dispensing unit 9 is arranged at the optical gas sensor 300 downstream of the gas admission element 8 in this gas-measuring arrangement 1 according to FIG. 1a. A quantity of liquid test substance 5 is dispensed by this test gas dispensing unit 9 from a test substance reserve 305, for example, from a tank 305 containing a reserve quantity 306. This quantity of test substance 5, injected in the liquid form, vaporizes, is atomized or evaporates in the gas sensor 300 to form a quantity of gaseous test substance 6, which is then located in the optical gas sensor 300 for the measurement.

The test gas dispensing unit 9 is actuated by means of a control line 91 by a control unit 3 such that a predefined quantity of liquid test substance 5 is dispensed into the optical gas sensor 300 upstream of the gas admission element 8 at predefined times $t_1$. In a preferred variant, the test gas dispensing unit 9 is configured as a piezo dispensing element. Such a piezo dispensing element is configured, combined with the test substance reserve 305, to dispense an exactly defined quantity of test substance each upon a single-time activation by means of a control signal 91' (FIGS. 2, 3), without deactivation of the piezo dispensing element, for example, by an additional control signal 91" (FIGS. 2, 3) or by an exactly defined duration of the control signal 91" (FIGS. 2, 3), thus defined by a time control 44 (FIG. 3), being necessary.

The control unit 3 receives measured signals 35, 38 from the optical gas sensor 300 and from the detector element in the optical gas sensor 300. Furthermore, the control unit 3 controls the infrared optical radiator in the optical gas sensor 300 by means of a control line 33. The measured signal 35, as well as a measured signal pattern 38 based on the measured signal 35 are transmitted by the control unit 3 to an output unit 80 by means of a data or signal line 92. The output unit 80 is configured to actuate an acoustic alarm generator, for example, a horn 40, or an optical alarm generator, for example, a lamp 50, by means of the signal and data line 92. Furthermore, the output unit 80 is configured by means of an interface 81 to transmit data, analysis results, sensor signals, data signals or processed measured signals 35, 38 to an analysis system 70 via signal and data lines 92 as well as control lines 91. A data bank 71, which can log states and events of tests of the gas-measuring arrangement 1, is preferably arranged in the analysis system 70. An operating and display unit (user interface) 60 is connected by the output unit 80 via a signal and data line 92. The operating and display unit 60 has a display screen 61, on which error messages as well as instructions for a user, as well as measured signals or measured values can be displayed. The control unit 3 and the test gas dispensing unit 9 cooperate in conjunction with a memory 32 arranged in the control unit 3 or with a memory 32 associated with the control unit 3 in a method for testing the gas-measuring arrangement 1, as is explained in more detail in FIGS. 2 and 3. The response of the optical gas sensor 300 to the dispensing of a quantity of liquid test substance 5 with evaporation of the quantity of liquid test substance 5 into a quantity of gaseous test substance 6 into the optical gas sensor 300 is used to check the time during which this dispensed quantity of test substance 5 diffuses again from the optical gas sensor 300 via the gas admission element 8. The control unit 3 performs for this a test procedure, as is seen more clearly in FIG. 3. It is determined by time measurement whether the dispensed quantity 5, 6 has escaped the optical gas sensor 300 after a certain time or not. If this dispensed quantity of test substance 5, 6 has not escaped from the optical gas sensor 300 after a predefined time, it can be inferred or determined by the control unit 3 that an incorrect situation is occurring at the gas admission element 8.

FIG. 1b shows a modified gas-measuring arrangement 1' compared to FIG. 1a. Instead of the optical gas sensor with an infrared multireflection cell 300, a catalytic gas sensor 301 is shown in FIG. 1b. Such a catalytic gas sensor 301, also known as heat tone sensor, is connected to a control unit 3 and to a test gas dispensing unit 9, similarly to what is described in FIG. 1a in connection with the optical gas sensor 300. Identical elements in FIGS. 1a and 1b are designated by the same reference numbers in FIGS. 1a and 1b.

The description of the functionality and the interaction of the control unit 3 with the test gas dispensing unit 9 can also be extrapolated, as is explained in connection with FIG. 1a, to the functionality of the interaction of the control unit 3 and the catalytic gas sensor 301 with inclusion of the test gas dispensing unit 9 for testing the gas admission element 8.

The elements shown in FIG. 1a, namely, the output unit 80, the analysis system 70 and the operating and display unit 60 with the corresponding additional elements, as well as the data lines 92, as well as control lines 91 are not shown in detail in FIG. 1b. It is, however, implied in the sense of the present invention that the gas-measuring arrangement 1' can interact with the analysis system 70, the analysis unit 80 and the operating and display unit 60 in a similar manner as is described in connection with FIG. 1a concerning the gas-measuring arrangement 1. The control lines 91 and data lines 92 are indicated schematically in a simplified manner only in this gas-measuring arrangement P.

Unlike in FIG. 1a with the gas-measuring arrangement 1, this gas-measuring arrangement 1' shown in FIG. 1b shows the aspect that another gas sensor system 30, configured as one or two catalytic measuring elements as a sensor-measuring arrangement, is arranged in the catalytic gas sensor 201, and if a special gas, for example, ethane, methane, butane or propane is fed, these elements engage in a chemical reaction with this gas. A part of the gas is consumed during this reaction at the catalytic measuring elements. This has the effect that a dispensed quantity of test substance 5, 6 will not escape completely into the measuring environment 2 after a predefined time through the gas admission element 8, but there is a shortage, which is due to the consumption of measured gas by the catalytically active measuring elements in the catalytic gas sensor 301. This effect is to be taken into account when testing the gas-measuring arrangement 1' or when testing the gas admission element 8 by means of the quantities of test substance 5, 6 entering by dispensing or diffusion and the escaping quantities of gas after a certain time. This is explained in more detail in FIG. 2 and the corresponding description.

FIG. 1c shows a gas-measuring arrangement 1" with an electrochemical gas sensor 302. Elements that are identical in FIGS. 1a, 1b and 1c are designated by the same reference numbers in FIGS. 1a, 1b and 1 c. Unlike in FIG. 1a with the gas-measuring arrangement 1, the gas-measuring arrangement 1" in this FIG. 1c shows the aspect that another gas sensor system 30, configured as a sensor-measuring arrangement, preferably comprising a liquid electrolyte and an arrangement of electrodes in the electrochemical gas sensor 302, is arranged. An electrochemical reaction or chemical reaction tales place at the electrodes when feeding a special gas, for example, ammonia. The gas-measuring arrangement 1" is shown in a similarly simplified manner as the gas-measuring arrangement 1' according to FIG. 1b. Comments made in connection with this simplified view in the description of FIG. 1a can also be extrapolated to this FIG. 1c. It should be noted concerning the interaction of the control unit 3 with the test gas dispensing unit 9 and with the electrochemical gas sensor 302 that a gas sensor system 30 with an electrochemical gas sensor 302 also consumes a certain quantity of test gas during the measurement, similarly to a catalytic gas sensor 301 according to FIG. 1b, due to the chemical reaction taking place at the electrodes. This should also be taken into account in this embodiment according to FIG. 1c when testing and setting up the balance of the dispensed quantities of test substance 5, 6 and the quantities of gas escaping through the gas admission element 8. This is described in more detail in FIG. 2 as well as in the description of FIG. 2.

FIG. 1d shows a gas-measuring arrangement 1'''. This gas-measuring arrangement 1''' has a semiconductor sensor 303 as a gas sensor system 30. The explanations given in connection with FIGS. 1a, 1b and 1c are correspondingly also applicable to FIG. 1d. The gas-measuring arrangement 1''' is explained in a simplified view comparable to FIGS. 1b and 1c. Identical elements in FIGS. 1a, 1b, 1c and 1d are designated by the same reference numbers in FIGS. 1a, 1b, 1c and 1d. The semiconductor sensor 303 is shown in FIG. 1d as a gas sensor system 30. The test gas dispensing unit 9 is shown as an interaction of a test substance reserve 305 with a valve 304 as another difference. This valve 304 is actuated by means of the control line 91 by the control unit 3. Similarly to what was described before in connection with FIGS. 1a, 1b, 1c, a reserve quantity 306 is contained in the test substance reserve 305. The reserve quantity 306 in this FIG. 1d is preferably a liquid gas, which is contained under pressure in the test substance reserve 305. When the valve 304 is opened for a predefined time, a portion of the reserve quantity 306 can enter the semiconductor sensor 303 from the test substance reserve 305. Depending on the value of the overpressure in the test substance reserve 305, a portion of the reserve quantity 306 enters the semiconductor sensor 303 as a quantity of liquid test substance 305 or as a quantity of already evaporated test substance 6. The transition from the liquid phase of the quantity of test substance 5 to the gaseous phase of the quantity of test substance 6 may take place directly due to pressure release when opening the valve 304, as well as when the quantity of liquid test substance 5 impinges on or impacts the walls of the semiconductor sensor 303. The interaction of the control unit 3 with the test gas dispensing unit 9 and the valve 304 and the test substance reserve 305 is described in detail in the description of FIG. 2 as well as in the process shown in FIG. 3 and in the corresponding description of the process according to FIG. 3.

Figure 2:
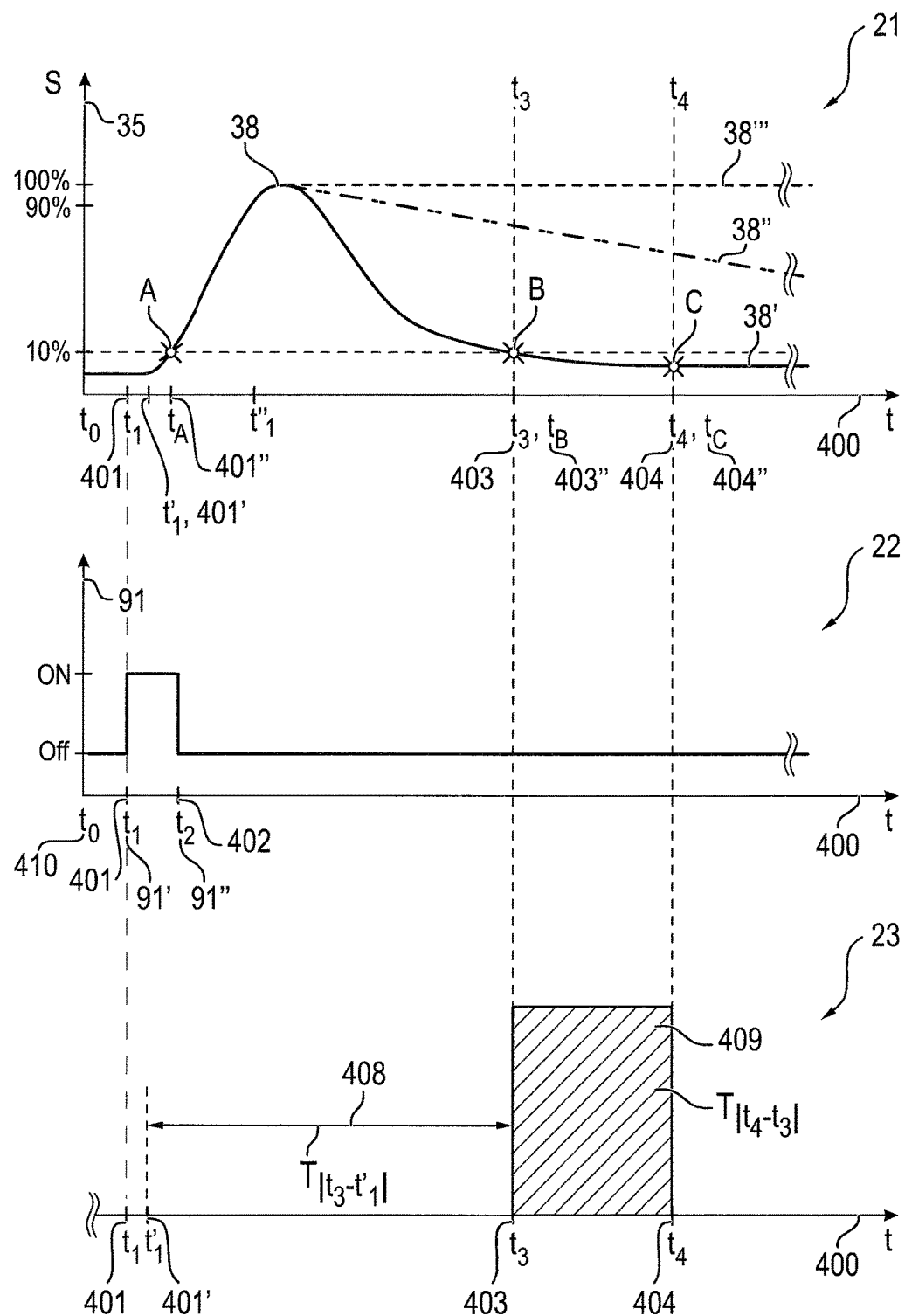
FIG. 2 is a graph of a typical course of a measured signal of a gas sensor during a testing with the testing device.

FIG. 2 shows a typical pattern of a measured signal of a gas-measuring arrangement with a gas sensor during a testing with a testing device. Three diagram portions 21, 22, 23 are shown, which represent each a time curve t 400 synchronized with one another.

A measured signal pattern 38, 38' and 38" is shown in an upper portion 21 of the diagram as a time curve of a measured signal S 35. The measured signal S 35 is scaled on the ordinate. The scaling is highlighted at 10%, 90% and 100%. The signal values, at which the measured signal 38 reaches a value of 10% of the measured signal amplitude S 35 of 100%, are shown in the signal pattern 38. These points are designated by A and B, respectively, in the pattern 38.

The percentage values 10%, 90%, 100% shown are advantageous for illustrating and explaining the signal characteristics of gas sensors, because temporal and dynamic properties of gas sensor can be in a uniform manner in this way and are thus comparable. The so-called $t_{10\text{-}90}$ rise time is suitable in measuring technology and is commonly used to characterize a rise time upon an increase in a gas concentration to 100% of the maximum range of measurement.

The so-called $t_{10\text{-}90}$ rise time is often also called sensor response time. The $t_{10\text{-}90}$ rise time corresponds to the duration of time during which the measured signals have values in a value range between 10% and 90% of the end value (100%) of the signal, which end value is due to the change in the gas concentration, during a signal rise phase.

The so-called $t_{90-10}$ decay time is obtained for this in a comparable manner upon a reduction of a gas concentration to 10% of the range of measurement for characterizing a signal decay. The $t_{90-10}$ decay time corresponds to the time during which the measured signals have values in a value range between 90% and 10% during a signal decay phase.

The pattern of a control signal 91 over the time t 400 is shown in the middle diagram portion 22. The control signal 91 is generated by the control unit 3 (FIGS. 1a, 1b, 1c and 1d, 3).

The lower diagram portion 23 shows a detail from the time curve t 400. Especially essential times, which are essential for the testing of the gas-measuring arrangement 1, 1', 1", 1''' (FIGS. 1a, 1b, 1c and 1d), are highlighted in this detail from the time curve t 400. The time curve t 400 of the essential times in the three diagrams 21, 22, 23 will now be described beginning with a time $t_0$ 410. The times having identical designations in the three diagrams 21, 22, 23 are always chronologically synchronous with one another. The time curve t 400 begins with a time $t_0$ 410, at which the gas-measuring arrangement 1, 1', 1", 1''' (FIGS. 1a, 1b, 1c and 1d) detects ambient air from the measuring environment 2 (FIGS. 1a, 1b, 1c and 1d).

The measured signal S 35 shows at the time $t_0$ 410 a base signal, which represents the absence of test gas or harmful gas.

A switching signal is sent by the control unit 3 (FIGS. 1a, 1b, 1c and 1d) to the test gas dispensing unit 9 (FIGS. 1a, 1b, 1c, 1d) at a time $t_1$ 401 in order to dispense or inject a quantity of test substance 5 (FIGS. 1a, 1b, 1c and 1d) to the gas sensor 300, 301, 302, 303 (FIGS. 1a, 1b, 1c and 1d) as a liquid quantity. The quantity of test substance 5 (FIGS. 1a, 1b, 1c and 1d) is evaporated into a quantity of gaseous test substance 6 (FIGS. 1a, 1b, 1c and 1d) at the time $t_1$' 401' and is thus available as a test gas for detection by the sensor-measuring arrangement by the gas sensor system 30 (FIGS. 1a, 1b, 1c and 1d). Based on the signal rise 38 of the measured signal 35, it can be assumed in this example with certainty at a time $t_1$", that is chronologically later than the time $t_1$', that quantities of gaseous test substance have reached the sensor-measuring arrangement (FIGS. 1a, 1b, 1c and 1d). The test gas dispensing unit 9 (FIGS. 1a, 1b, 1c and 1d) is again deactivated by another control signal 91' at the time $t_2$ 402, so that no additional quantity of test substance 5 (FIGS. 1a, 1b, 1c and 1d) is dispensed towards the gas sensor system 30 (FIGS. 1a, 1b, 1c and 1d). The measured signal S 35 responds to the dispensing of the quantity of test substance 6 (FIGS. 1a, 1b, 1c and 1d) with a signal rise. The signal rise corresponds to the current change in the gas concentration, caused by the quantity of dispensed gaseous test substance 6 (FIGS. 1a, 1b, 1c and 1d). The measured signal S 35 already has 10% of the initial amplitude at the time $t_A$, 401". The signal rise 38 following subsequently reaches an amplitude value of 90% approximately at the time $t_1$". In the meantime, the control signal 91" has already terminated the dispensing of the of test substance 5 (FIGS. 1a, 1b, 1c and 1d). The measured signal S 35 decays over time in case of unhindered inflow and outflow through the gas admission element 8 (FIGS. 1a, 1b, 1c and 1d). At the time $t_3$ 403, the measured signal decays in this view according to FIG. 2 below an amplitude of 10%. This amplitude value of 10% is plotted as a point B at a time $t_B$ 403" in the time curve 400. The measured signal S 35 has again reached the base signal seen prior to the dispensing of the quantity of test substance 5, 6 (FIGS. 1a, 1b, 1c and 1d) by means of the control signals 91', 91" at the time $t_4$ 404 or tC 404" with a corresponding value of the measured signal S 35, shown as a point C on pattern 38'.

A signal pattern 38''' is obtained in case the gas admission element 8 (FIGS. 1a, 1d) has a blockage or a clogging in the gas supply 7 (FIGS. 1a, 1d) in an optical gas sensor 300 (FIG. 1a) or in a semiconductor sensor 303 (FIG. 1d). A signal pattern 38" is obtained if the gas admission element 8 (FIGS. 1b, 1c) has a blockage in case of a catalytic gas sensor 301 (FIG. 1a) or in case of an electrochemical gas sensor 302 (FIG. 1c).

The middle diagram portion 22 shows the pattern of the control signal 91 over the time t 400. This time curve t 400 of the middle diagram portion 22 is shown synchronously with the time curve t 400 of the upper portion 21 of the diagram. Beginning from a time $t_0$ 410, a control signal 91' is activated at a time $t_1$ 401, and this control signal 91' brings about the dispensing of the quantity of test substance 5 (FIGS. 1a, 1b, 1c and 1d). The dispensing of the quantity of test substance 5 is deactivated at the time $t_2$ 402 (FIGS. 1a, 1b, 1c and 1d) by means of the control signal 91".

The lower diagram portion 23 of this FIG. 2 shows as a detail two highlighted time periods 408 and 409 in the time curve 400. These two time periods 408, 409 are relevant for the testing of the gas-measuring arrangement 1, 1', 1", 1' (FIGS. 1a, 1b, 1c and 1d) for arrangement in the time curve t 400. The process time 408 is the duration that is obtained in case of an unhindered inflow and outflow of gas from the measuring environment 2 (FIGS. 1a, 1b, 1c and 1d) through the gas admission element 8 (FIGS. 1a, 1b, 1c and 1d) to the gas sensor 30, 300, 301, 302, 303 (FIGS. 1a, 1b, 1c and 1d) according to the pattern 38' from the upper portion 21 of the diagram. The process time 408 is consequently a duration for the inflow and outflow, starting with the time $t_1$' 401', at which the transformation or evaporation of a quantity of liquid test substance 5 into the quantity of gaseous test substance 6 begins following the dispensing (FIGS. 1a, 1b, 1c and 1d) at the sensor-measuring arrangement (FIGS. 1a, 1b, 1c and 1d), until the outflow of the quantity of gaseous test substance 6 (FIGS. 1a, 1b, 1c and 1d) into the measuring environment 2 (FIGS. 1a, 1b, 1c, 1d and 3) through the gas admission element 8 (FIGS. 1a, 1b, 1c, 1d and 3). Effects of wind or changes in pressure in the measuring environment 2 (FIGS. 1a, 1b, 1c, 1d and 3) are a priori ignored in the selection of a suitable process time. The time $t_3$ 403 is obtained relative to the time 401' $t_1$' as a duration of the sensor response following the evaporation of the quantity of test substance 5 dispensed in the liquid form (FIGS. 1a, 1b, 1c and 1d) according to the pattern 38 as a signal rise from the upper portion 21 of the diagram until the dilution of the gas mixture contained in the gas sensor system 30 (FIGS. 1a, 1b, 1c and 1d) to a value corresponding to 10% of the amplitude of the measured signal S 35 according to the pattern 38' as a signal decay in case of unhindered outflow of gas into the measuring environment 2 (FIGS. 1a, 1b, 1c and 1d) from the upper portion 21 of the diagram. This value at 10% of the maximum amplitude of the measured signal S 35 is designated as point B in the upper portion 21 of the diagram. The process time 408 consequently corresponds to the time during which a quantity of test substance, dispensed as a quantity of liquid test substance 5 and then occurring in the form of a quantity of gaseous test substance 6 after transformation (FIGS. 1a, 1b, 1c and 1d) is active at the sensor-measuring arrangement and is no longer active.

The time 409 begins with the end of the above-described process time 408. It is shown in the diagrams 21, 23 that the duration of the inflow 7 (FIGS. 1a, 1b, 1c, 1d) of gas from the measuring environment 2 (FIGS. 1*a*, 1*b*, 1*c*, 1*d*) and the subsequent duration of the outflow of gas back into the measuring environment 2 (FIGS. 1*a*, 1*b*, 1*c*, 1*d*) together corresponds as a process time 408 to a sum of the signal rise phase and signal decay phase. It results from this in this example that the drop below the 10% amplitude value of the measured signal S 35 (point B) in the upper portion 21 of the diagram is located at the end of the process time 408 and within the expectancy time window 409, which describes a situation in which an unhindered supply with inflow and outflow to the gas admission element 8 (FIGS. 1*a*, 1*b*, 1*c* and 1*d*) is given.

An alternative for setting the beginning of the time 409 is possible, for example, by setting a two-fold response time as a value corresponding to the process time 408. Another alternative is made possible if the respective diffusion times for the inflow and outflow, as well as their sum are determined experimentally or by means of calculation on the basis of the practical embodiment of the gas admission element 8 (FIGS. 1*a*, 1*b*, 1*c* and 1*d*) in the gas-measuring arrangement 1, 1', 1", 1''' (FIGS. 1*a*, 1*b*, 1*c* and 1*d*) and the corresponding material properties (number of gas admission elements, pore size, area, diameter) are determined and correspondingly stored as a process time.

In the upper portion 21 of the diagram, the points B and C are plotted at the times $t_B$ 403" and tC 404", and they are located, purely accidentally, at the times $t_3$ 403 as well as $t_4$ 404. However, the drop below the 10% amplitude value may be given at any desired time in the expectancy time window 409. If this point B with 10% of the amplitude of the measured signal S 35 is in the expectancy time window 409 between the times $t_3$ and $t_4$, the control unit 3 (FIGS. 1*a*, 1*b*, 1*c* and 1*d*) may perform an analysis and infer that the testing was performed with a result that the gas admission element 8 (FIGS. 1*a*, 1*b*, 1*c* and 1*d*) is open sufficiently freely without blockages or contamination.

In the upper portion 21 of the diagram, the measured signal pattern 38" shows a pattern that belongs to a sensor-measuring arrangement with a catalytic gas sensor 301 or with an electrochemical gas sensor 302. A decaying measured signal S 35 is shown based on both a catalytic gas sensor 301 and electrochemical gas sensor 302 having a consumption of measured gas. As a result, the measured signal S 35 decays after dispensing even if no gas can escape from the gas sensor 30 (FIGS. 1*a*, 1*b*, 1*c* and 1*d*) into the measuring environment 2 (FIGS. 1*a*, 1*b*, 1*c* and 1*d*) or no gas can flow out. The pattern according to 38" thus shows a case in which a gas admission element 8 (FIGS. 1*a*, 1*b*, 1*c* and 1*d*) of a catalytic gas sensor 301 or of an electrochemical gas sensor 302 is closed towards the measuring environment 2 (FIGS. 1*a*, 1*b*, 1*c* and 1*d*) or is hindered in effecting gas exchange.

Figure 3:
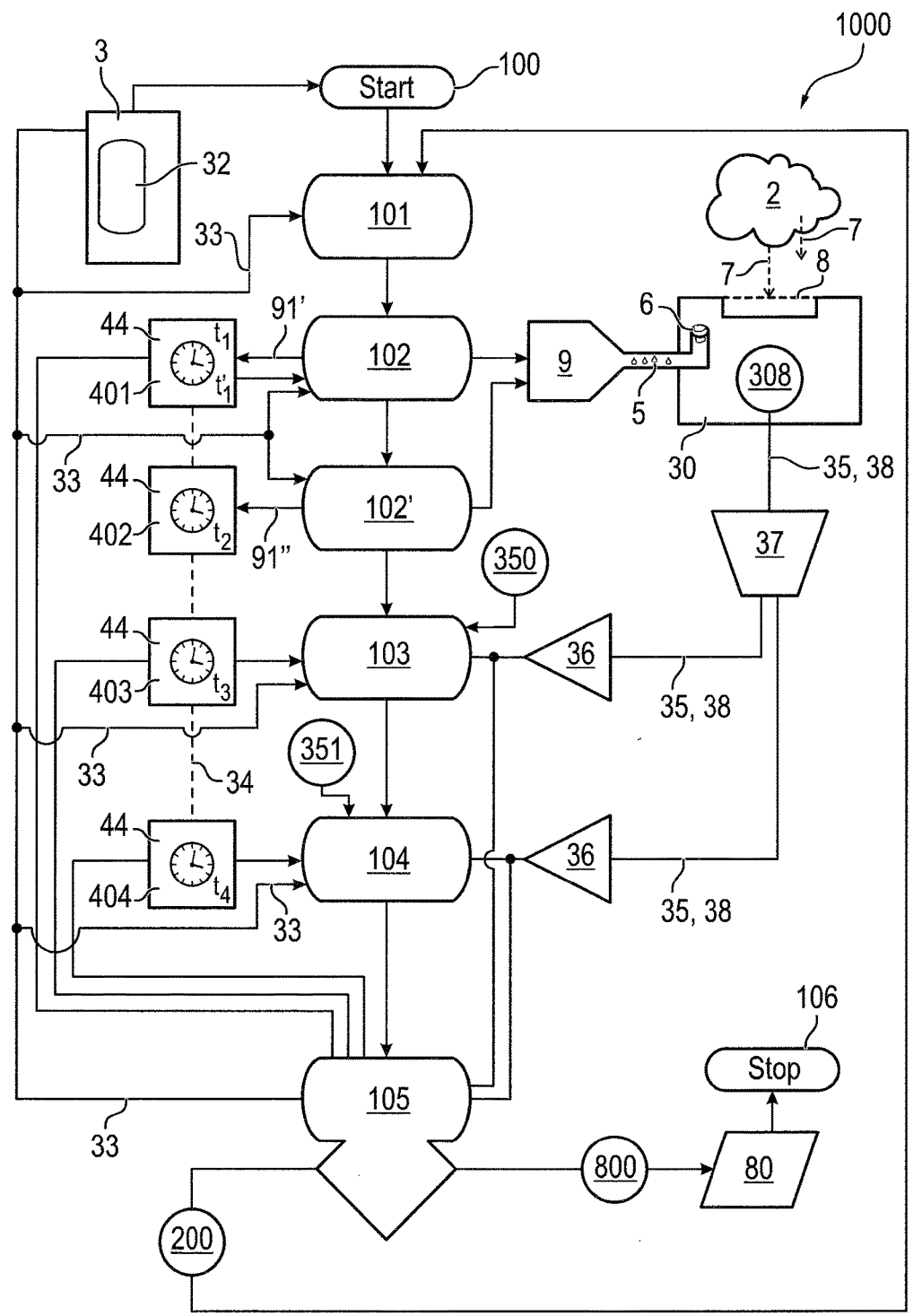
FIG. 3 is a flow diagram showing the course of testing of the gas sensor with the testing device.

FIG. 3 shows a flow chart 1000 for testing a gas-measuring arrangement 1, 1', 1", 1''' (FIGS. 1*a*, 1*b*, 1*c* and 1*d*) with a start 100 and with an end 106 (stop). The chart 1000 controls the sequence of five operating states 101, 102, 103, 104, 105 from start 100 to end 106. To control the chart 1000, the control unit 3 makes use of functionalities for time measurement, which are shown in this FIG. 3 as timer 44 assigned to the operating states 102, 102', 103 and 104. The control unit 3 acts on the operating states 101, 102, 103, 104, 105 as well as on the test gas source 9 via control signals, control lines 91, 91', 91" as well as control lines 33. The course of the times that are controlled by means of the timers 44 by the control unit 3 is symbolized by a synchronization signal 34.

The normal measuring operation is carried out with the gas sensor system 30 in the first operating state 101 (measuring operation) in a first step 101. Measured signals detected in the process are analyzed and displayed. The connections and elements needed for this are not shown in this FIG. 3. In the measuring operation 101, there is a gas supply (diffusion of ambient gas) 7 via a gas admission element 8 into a gas sensor 30 from a measuring environment 2 and in the gas sensor 30 to a sensor-measuring arrangement.

In a second operating state 102 (dispensing of test gas), the test gas source 9 is activated by the control unit 3 by means of a control line 33 in order to dispense a quantity of test substance 5, 6 to the gas sensor 30. A timer is activated now by the control unit 3 by means of a control signal 91' and a time $t_1$ 401 is thus marked. The time $t_1$ is stored in a memory 32 located in the control unit 3, so that it is available for the fifth operating state (case differentiation) 105. The evaporation needed for the transformation of the quantity of test substance 5 dispensed in the liquid form into a quantity of gaseous test substance 6 is likewise stored there as a time $t_1'$ 401', as is described in FIG. 1*a*. The second operating state 102 is followed by another step 102' as part of the second operating state 102, in which another control signal 91" is sent by the control unit 3 to the test gas source 9 in order to end the dispensing of the quantity of test substance 5 at a time $t_2$ 402. Provisions may be made in an embodiment of the test gas source 9 as a piezo dispensing element for omitting the second operating state 102' with the deactivation of the test gas source 9, because no deactivation signal 91" is necessary in the operating state 102 for controlling the dispensing by the piezo dispensing element. As another embodiment of dispensing with a piezo dispensing element, provisions may be made for setting a dispensing of the quantity of test substance by a sequence of drops. By presetting a predefined number of pulses acting on the piezo dispensing element, a number of drops corresponding to the number of pulses is dispensed as the quantity of test substance.

In a third operating state 103 (measured signal detection), a measured signal S 35, as well as a measured signal pattern 38 are detected by the system 30 on the basis of the dispensed quantity of test substance 5, 6. The measured signal S 35, as well as the measured signal pattern 38 are made available to the process 1000 and hence to the control unit 3 by means of a measured signal supply unit 37 and a signal transmission unit at a time $t_3$ 403, which is preset by the timer 44 in the third operating state 103, and the detected measured signal S 35 is compared to a first measured signal threshold value 350.

A further testing of the measured signal S 35 takes place in a next, fourth signal detection 104 at a predefined time $t_4$ 404, which follows the time $t_3$ 403, in a manner similar to that described in the third operating state 103, with a comparison of the detected measured signal S 35 with a second measured signal threshold value 351.

The values of the first measured signal threshold value 350 and of the second measured signal threshold value 351 are derived from a previously determined, typical signal characteristic of the sensor-measuring arrangement during the dispensing of the quantity of test substance 5, 6 with the test gas source 9 with unhindered outflow into the measuring environment 2 through the gas admission element 8. The response characteristic (rise time, e.g., $t_{10\text{-}90}$ rise time; decay time, e.g., $t_{90\text{-}10}$ decay time), which was already mentioned in connection with FIG. 2, the curve of the signal amplitude 35, 38 (zero signal, maximum signal amplitude) during unhindered inflow 7 through the gas admission element 8 to the measuring arrangement and unhindered outflow into the measuring environment 2 through the gas admission element 8 are also included here. A value with a lower signal amplitude compared to the value of the first measured signal threshold value 350 is selected now for the second measured signal threshold value 351, because a constellation with a signal decay 38', 38" (FIG. 2) is obtained in the pattern of the measured signal 38 during the expectancy time window 409 (FIG. 2) in case of hindered outflow of the dispensed quantity of test substance 5, 6 from the gas sensor 30 through the gas admission element 8 into the measuring environment 2.

In the fifth operating state (case differentiation) 105, the results of the comparisons of the measured signals 35 with the measured signal threshold values 350, 351 are analyzed with the aim of determining whether the measured signal 35 is below a threshold value 350, 351 over the pattern 38. If the comparison shows the result, the chart is branched into a first state of the gas sensor system 200, from which the measuring operation 101 is continued. The testing of the gas sensor 30 by means of the dispensed quantity of test substance 5, 6 is ended in this case with the positive result that the gas admission element 8 makes possible an unhindered inflow 7, i.e., that the gas admission element 8 is free from blockages. In case the result of the testing in the first operating state 105 is such that none of the threshold values 350, 351 has been undershot over the pattern 38 in an expectancy time window 409 (FIG. 2) formed by the times $t_4$ and $t_3$, the testing of the gas sensor system 30 has the result that the gas admission element 8 is supposedly blocked for the gas supply 7. The chart is branched in this case in a second state 800 of the gas sensor system 30, in which state the result of the testing is made available via an analysis unit 80 and the chart 1000 is subsequently ended 106 (stop).

While specific embodiments of the invention have been shown and described in detail to illustrate the application of the principles of the invention, it will be understood that the invention may be embodied otherwise without departing from such principles.

APPENDIX

List of Reference Designations 1, 1', 1", 1''' Gas-measuring arrangement, gas-measuring device
2 Measuring environment
3 Control unit, electronic unit
5 Quantity of test substance (liquid), injected
6 Quantity of test substance (gaseous), evaporated
7 Gas supply
8 Gas admission element
9 Test gas dispensing unit
21 First diagram
22 Second diagram
23 Third diagram
30 Gas sensor system
32 Memory (RAM, ROM)
33 Control line
35 Measured signal S, measured signal line
36 Signal transmission unit
38', 38", 38''' Measured signal pattern
37 Signal supply unit
40 Acoustic alarm generator (horn)
44 Timer/stop watch/chronometer
50 Optical alarm generator (lamp)
60 Operating and display unit (user interface)
61 Screen element
70 Analysis system
71 Data bank
80 Output unit
81 Interface
91, 91', 91" Control signal, control signal pattern, control line
92 Signal and data line, status signal or alarm signal
100 Start
101 First operating state (measuring operation)/step 1
102, 102' Second operating state (test gas dispensing)/steps 2, 2'
103 Third operating state (measured signal detection)/step 3
104 Fourth operating state (measured signal detection)/step 4
106 Fifth operating state (case differentiation)/step 5
106 Stop
200 First state of the gas sensor system
300 Optical gas sensor, IR multireflection cell
301 Catalytic gas sensor, heat tone sensor
302 Electrochemical gas sensor
303 Semiconductor gas sensor
304 Valve
305 Test substance reserve, tank, container, cylinder
306 Reserve quantity
  Sensor-measuring arrangement
350 First measured signal threshold value ($t_3$, $t_B$)
351 Second measured signal threshold value ($t_4$, tC)
400 x axis, time course t
401 Time $t_1$, activation time
401' Time $t_1'$
401" Time $t_0$
402 Time $t_2$, deactivation time
403 Time $t_3$
403" Time $t_B$
404 Time $t_4$
404" Time tC
408 Process time $T_{|3-t'|}$
  (Inflow+evaporation+outflow)
409 Expectancy window $T_{|t4-t3|}$
410 Time $t_0$
800 Second state of the gas sensor system
1000 Chart

What is claimed is:

1. A method for testing at least one gas admission element of a gas sensor or of a gas-measuring arrangement having at least one gas sensor, the method comprising the steps of:
  providing a control unit to control a sequence of operating states;
  with the control unit, beginning from a start time, bringing about a first operating state with a continuous measuring operation;
  with the control unit, bringing about, in a second operating state, a dispensing of a quantity of test substance, by means of a test gas dispensing unit arranged downstream of the gas admission element and upstream of the sensor-measuring arrangement, to a sensor-measuring arrangement arranged in the gas sensor;
  with the control unit, initiating a start of an expectancy time window, in a third operating state, with the control unit detecting at least one measured signal or a plurality of measured signals of the gas sensor with the beginning of the expectancy time window, and with the control unit comparing the at least one detected measured signal or one of a plurality of measured signals with a first measured signal threshold value;

with the control unit, detecting at least one additional measured signal or another plurality of measured signals of the gas sensor, in a fourth operating state, with the control unit comparing the at least one additional detected measured signal or one of the additional plurality of measured signals with a second measured signal threshold value, and the control unit initiating an end of the expectancy time window;

with the control unit, determining, on the basis of the comparison of the measured signal with the first measured signal threshold value or with the second measured signal threshold value or with both the first measured signal threshold value and the second measured signal threshold value, whether the gas admission element is ready to function for feeding air, gas or gas mixture from a measuring environment, in a fifth operating state; and with the control unit, determining an indicator of the readiness of the gas sensor to operate on the basis of the comparison of the measured signal with the first measured signal threshold value or with the second measured signal threshold value or with both the first measured signal threshold value and the second measured signal threshold value.

2. A method in accordance with claim 1, wherein the dispensing of the quantity of liquid test substance from the test gas dispensing unit to the sensor-measuring arrangement in the gas sensor is brought about by the control unit in the second operating state such that the control unit activates the test gas dispensing unit in a time course at a first, activation time.

3. A method in accordance with claim 1, wherein the dispensing of the quantity of liquid test substance by the test gas dispensing unit to the sensor-measuring arrangement in the gas sensor is brought about by the control unit in the second operating state such that the control unit activates the test gas dispensing unit for dispensing the quantity of liquid substance in a time course at a first, activation time, and that the control unit deactivates the dispensing of the quantity of liquid test substance by the test gas dispensing unit at a second, deactivation time, which is spaced from the first, activation time, following the latter in time.

4. A method in accordance with claim 3, wherein a size or a volume or both a size and a volume of the gas sensor is taken into account by the control unit for the second, deactivation time in the time course.

5. A method in accordance with claim 3, wherein:
a third time is determined or predefined by the control unit in the third operating state from the first, activation time in the time course, which is representative of the dispensing of the quantity of liquid test substance to the sensor-measuring arrangement or from a time which is derived from this first, activation time and which is representative of a transformation of the quantity of liquid test substance into a quantity of gaseous test substance at the sensor-measuring arrangement, which transformation took place in time after the dispensing such that the third time is spaced in time, for a process time, from the first, activation time or from the time derived from the first, activation time such the process time corresponds to an unhindered inflow from the measuring environment through the gas admission element to the sensor-measuring arrangement in the gas sensor and to a subsequent unhindered outflow from the gas sensor into the measuring environment or corresponds to a duration of the inflow and outflow.

6. A method in accordance with claim 5, wherein any combination of a size or a volume of the gas sensor, a number, a thickness, a pore size, an area or a diameter of the gas admission element is taken into account by the control unit for the third time in the time course.

7. A method in accordance with claim 5, wherein any combination of a size or a volume of the gas sensor, a number, a thickness, a pore size, an area or a diameter of the gas admission element is taken into account by the control unit for a fourth time in the time course, at which at least one additional measured signal or an additional plurality of measured signals are detected and compared with a second measured signal threshold value in the fourth operating state in the course of the expectancy time window.

8. A method in accordance with claim 1, wherein a size or a volume or both a size and a volume of the gas sensor is taken into account by the control unit when dispensing the portion of liquid test substance by means of the test gas dispensing unit.

9. A method in accordance with claim 1, wherein a substitute signal is provided by the control unit in the third, fourth and fifth operating states for a time of an interruption of the continuous measurement.

10. A method in accordance with claim 1, wherein a determination or a provision or both a determination and a provision of a status signal is performed by the control unit on a basis of the comparison in the fifth operating state.

11. A method in accordance with claim 10, wherein the status signal is provided by the control unit for an output unit, a central analysis system, a central alarm unit or a mobile output device.

12. A method in accordance with claim 10, wherein an alarm signal or a message is outputted by the output unit, the central analysis system, the central alarm unit or the mobile output device.

13. A method in accordance with claim 12, wherein the alarm signal is provided by the control unit or by the output unit or by both the control unit and by the output unit for an acoustic alarm generator for generating an acoustic alarm or for an optical signal generator for generating an optical or visually visible alarm.

14. A method in accordance with claim 12, wherein the message is provided by the control unit or by the output unit or by both the control unit and by the output unit on a display unit, screen as an instruction in a visible form as a warning message or an instruction in text form, graphic form or in a symbolic form.

15. A gas-measuring device comprising:
at least one gas sensor with at least one sensor-measuring arrangement, wherein the gas sensor or the gas-measuring arrangement detects a gas concentration or a change in a gas concentration and comprises a gas admission element arranged upstream of the sensor-measuring arrangement;
a test gas dispensing unit arranged downstream of the gas admission element in the gas sensor or in the gas-measuring arrangement; and
a control unit and memory associated with the control unit wherein the control unit is configured to:
beginning from a start time, bring about a first operating state with a continuous measuring operation;
bring about, in a second operating state, a dispensing of a quantity of test substance, by means of a test gas dispensing unit arranged downstream of the gas admission element and upstream of the sensor-measuring arrangement, to a sensor-measuring arrangement arranged in the gas sensor;

initiate a start of an expectancy time window, in a third operating state, with the control unit detecting at least one measured signal or a plurality of measured signals of the gas sensor with the beginning of the expectancy time window, and with the control unit comparing the at least one detected measured signal or one of a plurality of measured signals with a first measured signal threshold value;

detect at least one additional measured signal or another plurality of measured signals of the gas sensor, in a fourth operating state, with the control unit comparing the at least one additional detected measured signal or one of the additional plurality of measured signals with a second measured signal threshold value, and the control unit initiating an end of the expectancy time window;

determine on the basis of the comparison of the measured signal with the first measured signal threshold value or with the second measured signal threshold value or with both the first measured signal threshold value and the second measured signal threshold value, whether the gas admission element is ready to function for feeding air, gas or gas mixture from a measuring environment, in a fifth operating state; and determine an indicator of the readiness of the gas sensor to operate on the basis of the comparison of the measured signal with the first measured signal threshold value or with the second measured signal threshold value or with both the first measured signal threshold value and the second measured signal threshold value.

16. A gas-measuring device in accordance with claim 15, wherein the test gas dispensing unit comprises:

a piezo dispensing element; and a reservoir fluidically connected to the piezo dispensing element for storing a reserve quantity, wherein the control unit is configured to activate the piezo dispensing element at a first time.

17. A gas-measuring device in accordance with claim 15, wherein the test gas dispensing unit comprises:

a valve; and a reservoir fluidically connected to the valve for storing a reserve quantity, wherein the control unit is configured to activate the valve at a first time and to deactivate the valve at a second time.

18. A gas-measuring device in accordance with claim 15, further comprising:

an output unit;

an optical alarm generator or an acoustic alarm generator or both an optical alarm generator or an acoustic alarm generator, wherein the optical alarm generator or the acoustic alarm generator or both the or both the optical alarm generator and the acoustic alarm generator are provided and configured for outputting an alarm signal in interaction with the control unit or with the output unit or with both the control unit and the output unit.

19. A gas-measuring device in accordance with claim 18, further comprising an analysis system wherein:

the output unit has an interface; and the interface is configured and provided for transmitting the status signal to an analysis system in interaction with control unit.

20. A gas-measuring device in accordance with claim 15, wherein the at least one sensor-measuring arrangement is configured:

as a combination of electrodes and an electrolyte in an electrochemical gas sensor, as a combination of a radiation source and a detector element in an infrared optical gas sensor;

as a combination of catalytically active measuring elements or catalytically passive measuring elements in a catalytic gas sensor or both catalytically active measuring elements and catalytically passive measuring elements in a catalytic gas sensor or a heat tone sensor; or as gas species-specific and sensitive semiconductor elements in semiconductor gas sensor.

* * * * *